United States Patent [19]
van't Hooft

[11] Patent Number: 4,881,938
[45] Date of Patent: Nov. 21, 1989

[54] METHOD AND AN APPARATUS FOR TREATING A PART OF THE BODY WITH RADIOACTIVE MATERIAL

[76] Inventor: Eric van't Hooft, Gezichtslaan 16, 3956 BB Leersum, Netherlands

[21] Appl. No.: 17,036

[22] Filed: Feb. 18, 1987

Related U.S. Application Data

[63] Continuation of Ser. No. 689,781, Jan. 8, 1985, abandoned.

[30] Foreign Application Priority Data

Jan. 12, 1984 [NL] Netherlands .......................... 8400108

[51] Int. Cl.⁴ ...................... A61N 5/10; A61M 37/04; G21F 5/02
[52] U.S. Cl. ...................................... 600/3; 250/497.1
[58] Field of Search .................................. 128/1.1, 1.2; 250/497.1; 600/3

[56] References Cited

U.S. PATENT DOCUMENTS

| | | | |
|---|---|---|---|
| 2,750,517 | 6/1956 | Baum | 128/1.2 |
| 2,947,194 | 8/1960 | Shimanckas | |
| 3,088,032 | 4/1963 | Brunton | |
| 3,669,093 | 6/1972 | Sauerwin et al. | 128/1.1 |
| 3,861,380 | 1/1975 | Chassagne et al. | |
| 4,233,517 | 11/1980 | van't Hooft | 600/3 |
| 4,427,005 | 1/1984 | Tener | 128/1.2 |

FOREIGN PATENT DOCUMENTS

| | | | |
|---|---|---|---|
| 0012004 | 6/1980 | European Pat. Off. | 128/1.2 |
| 1491728 | 6/1969 | Fed. Rep. of Germany | 128/1.2 |
| 2717341 | 11/1977 | Fed. Rep. of Germany | 128/1.2 |
| 479311 | 11/1969 | France | 128/1.2 |
| 0649412 | 3/1979 | U.S.S.R. | 128/1.2 |
| 1027078 | 4/1966 | United Kingdom | |

OTHER PUBLICATIONS

"Micro Selection LDR/MDR", Nucleatron brochure, Nucletron Trading BV, The Netherlands.
Lillicrop et al, Brit. Jour. of Rad., vol. 47, No. 559, Jul. 1974, pp. 425–426.

*Primary Examiner*—Francis Jaworski
*Assistant Examiner*—John C. Hanley
*Attorney, Agent, or Firm*—Griffin, Branigan & Butler

[57] ABSTRACT

A method and an apparatus for treating a part of the body of a patient with radioactive material, in which at least one hollow needle is introduced into the part of the body concerned, said needle being capable of subsequently receiving a tube containing selectively positioned radioactive material, previously arranged therein. Use is made of a cart comprising at least one tube containing selectively positioned radioactive material, an intermediate container for shielding the tube or tubes, and apparatus for transporting the said tube with radioactive material into and out of the shielding means. According to the present invention, each implant needle is connected to the cart by means of a patient transfer tube with a patient connector and a machine connector connected with a plurality of external tubes, from which cart tubes are selectively inserted into the needle or needles already introduced by means of one or more transport threads movable in the patient transfer tubes.

15 Claims, 3 Drawing Sheets

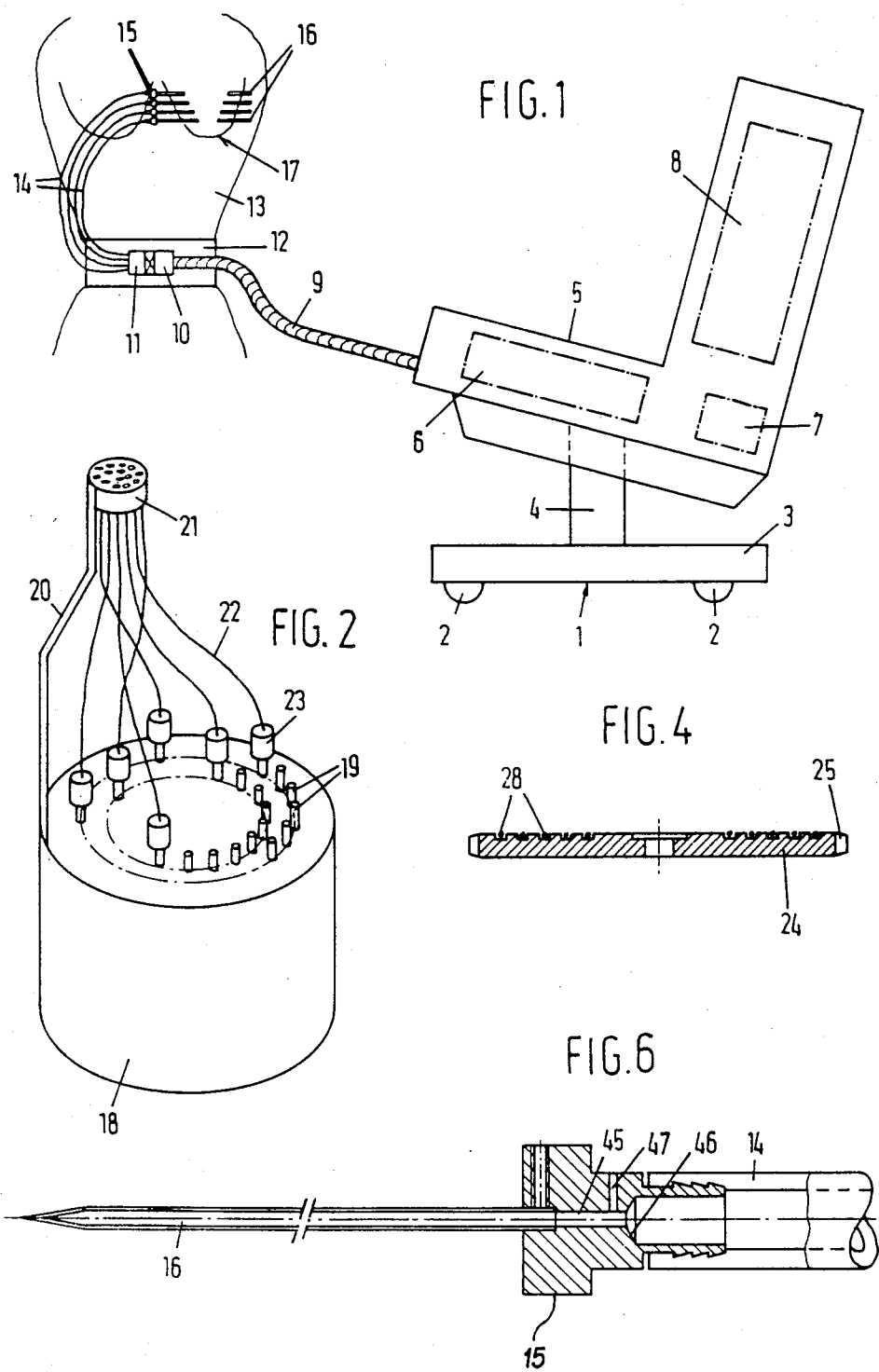

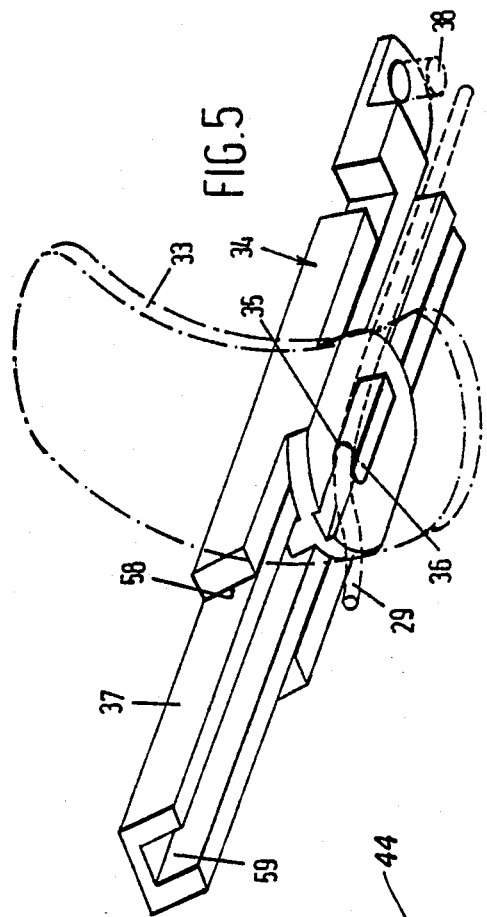
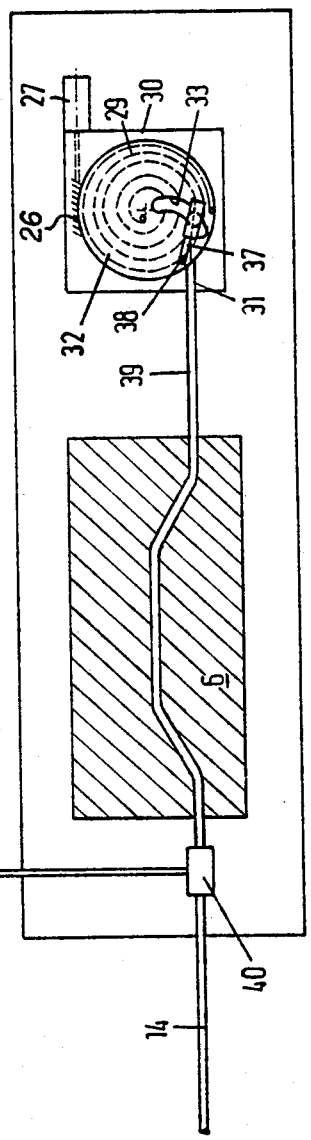
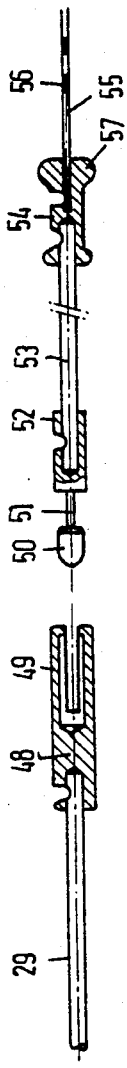

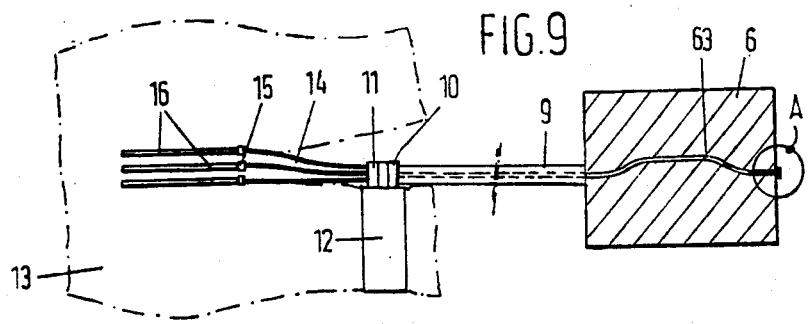
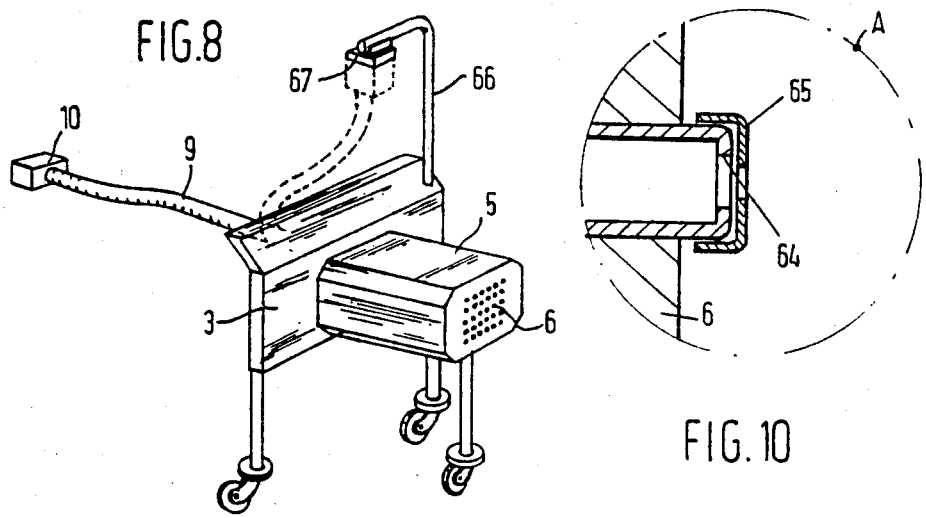
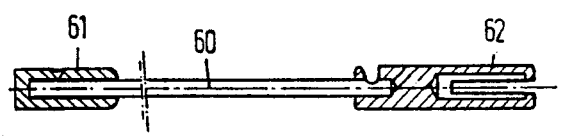
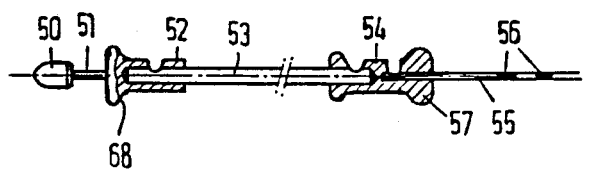

METHOD AND AN APPARATUS FOR TREATING A PART OF THE BODY WITH RADIOACTIVE MATERIAL

This application is a continuation of application Ser. No. 689,781, filed Jan. 8, 1985, now abandoned.

BACKGROUND OF THE INVENTION

This invention relates to a method of treating a part of the body of a patient with radioactive material, in which at least one hollow needle is introduced into the part of the body concerned, said needle being capable of subsequently receiving a tube containing selectively positioned radioactive material previously arranged therein, while using a cart comprising at least one tube containing selectively positioned radioactive material, an intermediate container for shielding the tubes and means for transporting the said tube with radioactive material into and out of the shielding means.

SUMMARY OF THE INVENTION

It is an object of the present invention to improve such a generally known method.

To this end, the method according to the invention is characterized in that each implant needle is connected to the cart by means of a patient transfer tube having a patient connector and a machine connector connected with a plurality of external tubes, from which cart tubes are selectively inserted into the needle or needles already introduced.

The positioning can take place by means of a transport thread movable in the patient transfer tubes and the final position can be detected pneumatically by shutting off an air passage bounded by a shoulder, by means of a control head attached to each tube. This enables a highly accurate positioning of the radioactive material without the risk for the operator to be exposed to radiation.

A further improvement is obtained when the machine connector can be connected to a container connector of a storage container from which tubes can be selectively shifted into the cart.

The present invention further relates to a cart for use in the performance of the above described method, said cart being fitted with an intermediate container having a plurality of curved passages, there being arranged behind each passage a drive mechanism and a control mechanism.

The drive mechanism may comprise a drivable disc having a spiral groove, said groove accommodating a transport thread whose front end is adapted for coaction with a member, e.g. a tube, containing selectively positioned radioactive material, previously arranged therein.

In order to connect the transport thread to the tube with radioactive material the transport thread may have a gripper adapted for detachably receiving a head connected to one end of the tube.

A proper guidance of the transport thread is obtained when the disc is accommodated in a housing, one sidewall of which is fitted with a curved radial slot receiving a support having a transport thread guide channel, said support being arranged to be guided by the groove by means of a rotary arm mounted on the housing.

The support may be provided at its bottom with a tongue or lip adapted for coaction with the spiral groove in the disc. The arm may have a transport thread guide channel at the side facing the disc.

The drive of the disc can be effected by fitting the outer circumference of the disc with worm wheel teeth adapted for coaction with a drivable worm arranged within the housing.

The present invention further relates to the drive mechanism per se described hereinbefore.

With the cart described in the above, the positioning of the radioactive material takes place by means of a drive mechanism having a motor and being remotely controlled. A substantial simplification of the apparatus is obtained when use is made of a cart having an intermediate container fitted with a plurality of bent passages, which are continuous and through which can be moved a transport thread, one end of which is fitted with a pusher and the other end with a pulling member or gripper adapted for detachably receiving a head connected to one end of the tube with radioactive sources, while a control head attached to each tube is adapted for coaction with a shoulder of the needle: accordingly, this apparatus does not have a drive mechanism and the tubes with sources are positioned substantially manually.

By having the length of the flexible thread correspond substantially with the length of the patient transfer tubes, it is possible after the retraction of the transport thread and the disconnection of the machine connector and the patient connector, to provide the free end of the latter with a cover: As a result, the flexible thread and hence the tube with radioactive sources is fixedly confined on the one hand by the control head and on the other hand by the head between a stop of the needle connector on the one hand and the said cover on the other hand.

A proper attachment of the flexible thread and the tube with radioactive sources, fixedly connected to the thread, within the intermediate container is ensured by providing the free end of each passage in the intermediate container with a restriction through which the head but not the shoulder of the flexible rod can be moved, the rod linking up with the said projecting head being adapted for coaction with a blocking bracket.

The method and apparatus according to the invention have the advantage that the radioactive material can be brought accurately and without the risk of contamination of the operator, at the proper place in the body of a patient.

BRIEF DESCRIPTION OF THE DRAWING

One embodiment of an apparatus for treating the part of a body with radioactive material will now be described, by way of example, with reference to the accompanying drawings, in which:

FIG. 1 is a diagrammatic side view of an apparatus for treating the part of a body with radioactive material;

FIG. 2 shows a storage container employed when using the apparatus shown in FIG. 1;

FIG. 3 shows an enlarged detail of the apparatus shown in FIG. 1;

FIG. 4 shows an enlarged detail of the drive mechanism of the apparatus;

FIG. 5 shows a perspective bottom view of the guide;

FIG. 6 shows an enlarged detail of the apparatus shown in FIG. 1;

FIG. 7 shows the enlarged transport thread with coupling elements used in the apparatus shown in FIGS. 1-6 for transporting radioactive material;

FIG. 8 is a perspective view of a second embodiment of the apparatus according to the invention;

FIG. 9 is a diagrammatic top view of a part of the apparatus shown in FIG. 8 when in operation;

FIG. 10 shows the enlarged detail A of the apparatus shown in FIG. 9;

FIG. 11 is a diagrammatic side view of a transport thread used in the apparatus shown in FIGS. 8 and 9, and FIG. 12 is a diagrammatic side view of a flexible rod with a tube carrying the radioactive material.

DESCRIPTION OF THE PREFERRED EMBODIMENTS

As shown in FIGS. 1-7, an apparatus for treating the part of a body with radioactive material comprises a cart 1 with wheels 2 supporting a base 3 whereon a leg 4 is mounted. Leg 4 carries a housing wherein, diagrammatically shown, there are arranged an intermediate container 6, a drive mechanism 7 and a control mechanism 8. The intermediate container connects to an external tube 9 whose free end is fitted with a machine connector 10. Said machine connector 10 is adapted for coaction by means of locking members, not shown, with a patient connector 11 affixed to a patient belt 12 disposed on the body 13 of a patient to be treated. From the patient connector, there extend a plurality of patient transfer tubes 14, the ends of which are connected through needle connectors 15 to implant needles 16 disposed in a breast 17 of the patient.

The means necessary for treating a patient with radioactive material further comprise a storage container 18 (see FIG. 2), which is fitted at the top with a plurality of connectors 19 connecting to the passages, not shown, provided within the storage container, said passages each containing a tube with radioactive material. Storage container 18 is further provided with a support 20 to which there is attached a container connector 21 corresponding with the patient connector 11. The openings in the container connector 21 connect to the bottom of a plurality of selection tubes 22 whose free ends are fitted with selection tube connectors 23 adapted for coaction with connectors 19.

As shown in FIGS. 3, 4 and 5, the drive mechanism 7 comprises a disc 24 whose circumference has teeth 25 adapted for coaction with a worm 26, driven by a motor 27. The disc 24 is fitted at its top surface with a spiral groove 28 receiving a transport thread 29. Disc 24, worm 26 and motor 27 are received in a housing 30, not shown in FIGS. 4 and 5 for the sake of clarity. Housing 30 contains an outlet 31 for the transport thread 29.

To ensure a proper discharge of the transport thread from the spiral groove 28 via the opening 31, there is provided in an upper plate 32 for the disc 24 a radial slot 33 wherein a support 34 can move (see the perspective bottom view shown in FIG. 5).

Support 34 is fitted with a guide channel 35 for the transport thread. As shown in FIG. 5, the support is fitted at the bottom with a lip 36 extending into the groove 28 of the disc, thus ensuring a proper guiding by the support.

The support is fitted at the top with a slot 58 wherein a guide arm 37 is disposed whose one end is rotatably mounted on a shaft 38, which adjacent outlet 31 is attached to the upper plate 32. Furthermore, the guide arm 37 is fitted at the bottom with a groove 59 whose one end connects to the guide channel 35 in the support 34, its other end connecting to the outlet 31 in the housing.

As further shown in FIG. 3, the outlet 31 connects to a tube 39, which extends with a bent portion through the intermediate container 6. The other end of the tube 39 connects via a coupling 40 to a patient transfer tube 14. A number of such patient transfer tubes 14 are received in the external tube 9 (see FIG. 1): It is observed in this respect that the patient transfer tubes disposed on the body of the patient to be treated and those, contained in the external tube 9 are indicated by the same reference numeral, since the same patient transfer tubes are concerned here which are interconnected through machine connector 10, and the patient connector 11, respectively.

As shown in FIG. 3, the coupling 40 connects to a tube 41, which is connected to the pressure vessel 43 by means of a valve 42. Tube 41, upstream of the valve 42, is connected to a pressure transducer 44.

As shown in FIG. 6, the open end of the implant needle 16 is fitted in the needle connector 15, having a bore 45 fitted with a shoulder 46. Furthermore, bore 45 is also connected to an outlet 47.

FIG. 7 finally shows the free end of the transport thread 29, fitted with a gripper or similar crimp element 48 having gripper arms 49. Said arms 49 are adapted for coaction with a head 50 connected through a rod 51, a crimp element 52, a flexible rod 53 and a crimp element 54, to a tube 55 accommodating a plurality of radioactive sources 56. Crimp element 54, at the side facing the tube 55, is fitted with a control head 57 adapted for coaction with shoulder 46 disposed in the needle connector 15 (see FIG. 6).

The apparatus is operated as follows.

When a patient has to be treated, after the required data have been entered into the control mechanism in a known manner, the cart is moved to the storage container 18 and the machine connector 10 is connected to the container connector 21. Subsequently, the selection tube connectors 23 ar connected to the desired connectors 19. Then, the motor 27 of the drive mechanism 7 is put into operation, so that the transport thread 29 is moved out of the housing, with the gripper arm 49 at its front end in forward direction, via patient transfer tube 14, machine connector 10, container connector 21, the chosen selection tube 22, selection tube connector 23, connector 19 into storage container 18. During this forward movement of the transport thread, an automatic coupling takes place between the gripper arms 49 and the head 50 of the tube 55 chosen, after which the transport thread 29 is retracted until the tube 55 is present in the intermediate container 6. After all desired tubes 55 filed with radioactive sources 56 have thus been introduced in the intermediate container 6, the machine connector 10 is detached from the container connector 21, the cart 1 is moved close to the patient and then the machine connector 10 is coupled to the patient connector 11.

The motor 27 is now restarted so as to move the transport thread with a tube containing radioactive sources on its free end in forward direction via patient transfer tube 14 received in external tube 9, machine connector 10, patient connector 11, patient transfer tube 14 on the body of the patient, needle connector 15 into implant needle 16 disposed in the breast 17 of the patient. By opening valve 42, air is introduced from pressure vessel 43 via tube 41 and coupling 40 into patient transfer tube 14: The air flows along the transport thread and escapes via outlet 47. However, as soon as control head 57 contacts shoulder 46, the pressure in tube 41 will increase, which is recorded by pressure transducer 44. Pressure transducer 44 is in communication via means not shown, with motor 27 and will cause the latter to stop when the pressure in tube 41 increases due to the abutment of control head 57 against shoulder 46. This naturally implies that tube 55 with radioactive sources 56 is at its proper place in implant needle 16.

After treating the patient, the motor 27 is re-energized so that the transport thread is again wound on disc 24 until each tube 55 filled with radioactive material is present in the intermediate container 6 and can be clamped therein. Subsequently, cart 6 is moved to storage container 18, after which tubes 55 filled with radioactive material are returned to the storage container in a manner obvious after the foregoing.

In the above described manner, there is obtained an entirely closed transport system for the flexible transport thread, so that each time an accurate positioning of the tube 55 filled with radioactive material is possible without the risk of contamination of the operator.

Although nothing has been said in the above on given numbers of patient transfer tubes, transport threads, selection tubes, and the like, use is made in practice of a cart having an intermediate container accommodating 15 tubes. The number of patient transfer tubes 14 corresponds therewith. The storage container 18 may be provided with 45 connectors with communicating tubes for receiving therein a tube containing a source. It will be clear that the number of selection tubes in this case is also 15.

The second embodiment of the apparatus according to the invention, shown in FIGS. 8–12, comprises a great many elements that correspond with those of the above described first embodiment: Corresponding parts are indicated by the same reference numerals. The perspective view illustrated in FIG. 8 shows a base 3 which, true, differs from that shown in FIG. 1, but which basically comprises the same elements. On the base there is mounted a housing 5 containing an intermediate container 6. The ends of the tubes 63 disposed in the intermediate container are basically freely accessible. Furthermore, the front of the intermediate container 6 connects to an external tube 9 whose free end is fitted with a machine connector 10.

On the base 3, there is also provided an arm 66 whose free end is fitted with means 67 for retaining, in case of non-use, machine connector 10 (shown in striped fashion in FIG. 8).

In the diagrammatic view shown in FIG. 9, the intermediate container 6 is only one of the 45 tubes 63. Said tubes connect to an external tube 9 accommodating a number of patient transfer tubes, not further indicated, corresponding with the number of tubes, which patient transfer tubes terminate in machine connector 10. Said machine connector is adapted for coaction with patient connector 11 affixed to the patient belt 12 disposed on a leg of the patient 13 to be treated. From the patient connector there extend a plurality of patient transfer tubes 14 whose ends are connected through needle connectors 15 to implant needles 16 introduced into the patient's uterus, not further indicated.

As shown in FIG. 10, each tube 63 may be fitted at its free end with a restriction 64 through which can pass the head 50 but not the shoulder 68 of crimp element 52 (see FIG. 12): In this position rod 51 is adapted for coaction with a blocking bracket 65, which may have any form but which may be provided e.g. with a slotted opening of varying slot width.

As further shown in FIG. 11, for displacing the flexible rod 53 and the tube 55 with radioactive sources 56, use is made of a manual transport thread 60, one end of which is fitted with a pusher 61 and the opposite end with a gripper 62, which is basically identical to the gripper 48 (see FIG. 7).

Since the operation of the apparatus will be clear after the above, this will not be further described herein.

It is finally observed that a great many modifications are possible without departing from the scope of the present invention.

What I claim:

1. An apparatus for delivering at least one assembly of radioactive source material to a site in a human body for radioactive therapy, comprising:
   (1) an applicator having a first end and an opposite end, said first end being at least in part disposable inside the human body at the site intended for therapy and capable of receiving an assembly of radioactive source material, and said opposite end being disposable outside of the human body;
   (2) an applicator connector having a first end, a second end and a passageway extending therebetween and capable of passing a said assembly therethrough, said applicator connector being affixed at the first end thereof to the said opposite end of the applicator;
   (3) a container for storing at least one said assembly and having at least one container passageway therethrough;
   (4) a transfer tube means disposed between said container and said applicator connector with one end thereof connected to said second end of the applicator connector;
   (5) coupling means for coupling the other end of the transfer tube means to said container passageway;
   (6) transfer thread means attached at one end to an assembly of radioactive source material for transferring said assembly from the container to said applicator;
   (7) drive means connected to the other end of the transfer thread means for driving said transfer thread means;
   (8) control head means attached to said assembly that is capable of being sensed by a sensing means, and sensing means for sensing when the control head means is positioned such that said attached assembly is positioned in said applicator;
   (9) control means responsive to said sensing means such that when the assembly is in said position in said applicator, said control means interrupts said drive means, and further driving of said transfer thread cases.

2. An apparatus for delivering at least one assembly of radioactive source material to a site in a human body for radioactive therapy, comprising:
   (1) an applicator having a first end and an opposite end, said first end being at least in part disposable inside the human body at the site intended for therapy and capable of receiving an assembly of radioactive source material, and said opposite end being disposable outside of the human body;
   (2) an applicator connector having a first end, a second end and a passageway extending therebetween and capable of passing a said assembly therethrough, said applicator connector being affixed at the first end thereof to the said opposite end of the applicator and having near the second end thereof a shoulder in said passageway;

(3) a container for storing at least one said assembly and having at least one container passageway therethrough;

(4) a transfer tube means disposed between said container and said applicator connector with one end thereof connected to said second end of the applicator connector;

(5) coupling means for coupling the other end of the transfer tube means to said container passageway;

(6) pressurized fluid means for providing a source of pressurized fluid having communication means for providing pressurized fluid to the applicator connector passageway and having a pressure sensing means for sensing the fluid pressure in the applicator connector passageway;

(7) outlet means disposed between said first end and shoulder of the applicator connector and being in fluid communication with said applicator connector passageway and the atmosphere, wherein pressurized fluid in said applicator connector passageway is released to the atmosphere through said outlet when said outlet is in fluid communication with said shoulder and the pressure of the pressurized fluid in the said passageway remains at a preset low value;

(8) transfer thread means attached at one end to an assembly of radioactive source material for transferring said assembly from the container to said applicator;

(9) drive means connected to the other end of the transfer thread means for driving said transfer thread means;

(10) a control head connected to said assembly and being in a configuration such that when a said assembly is driven from said container by said transfer thread means and disposed in the applicator, the control head abuts said applicator connector shoulder and closes the fluid communication between said shoulder and said outlet, whereby the pressure of the pressurized fluid in the said applicator connector passageway rises;

(11) control means responsive to said pressure sensing means such that when the pressure of the pressurized fluid in the applicator connector passageway rises to a preset value, said control means interrupts said drive means, and further driving of said transfer thread ceases.

3. The apparatus of claim 2 wherein the applicator is in the form of a hollow needle.

4. The apparatus of claim 2 wherein the pressurized fluid communication means is in fluid communication with said coupling means and the pressurized fluid is disposable in said applicator connector passageway through said transfer tube means.

5. The apparatus of claim 4 wherein the said communication means has disposed therein a valve for controlling the flow of pressurized fluid.

6. The apparatus of claim 5 wherein the pressure sensing means is a pressure transducer.

7. The apparatus of claim 2 wherein the transfer tube means is in the form of an elongated, flexible transfer tube and the transfer tube has disposed between the container and the applicator connector a patient connector.

8. The apparatus of claim 7 wherein the patient connector is attachable to the human body intended for therapy.

9. The apparatus of claim 8 wherein the patient connector is attachable to the human body by being disposed on a belt means which is wrappable around a part of the human body and attachable thereto.

10. The apparatus of claim 9 wherein the patient connector is in two parts, one of which is affixed to said belt means and one of which is affixed to said transfer tube.

11. The apparatus of claim 10 wherein a portion of the transfer tube is disposed between and connected to the said patient connector and the said applicator connector.

12. The apparatus of any one of claims 1 through 11 wherein there are a plurality of applicators, applicator connectors, container passageways, transfer tube means, transfer thread means and drive means.

13. The apparatus of either claim 1 or claim 2 wherein the drive means comprises a disc with a spirally curved groove disposed in one surface thereof for receiving the transfer thread means, a worm gear disposed tangentially to the periphery of the disc and co-acting with teeth disposed on the periphery of the disc for driving the disc at its periphery, a housing enclosing said disc and a housing outlet for said transfer thread means.

14. The apparatus of claim 61 wherein said worm gear is driven by a motor and said control means interrupts said drive means by stopping said motor.

15. The apparatus of any one of claims 2 through 11 wherein the pressurized fluid means is a pressurized air means.

* * * * *